United States Patent
Baxter et al.

(10) Patent No.: US 6,706,719 B1
(45) Date of Patent: *Mar. 16, 2004

(54) HYDROXAMIC AND CARBOXYLIC ACID DERIVATIVES HAVING MMP AND TNF INHIBITORY ACTIVITY

(75) Inventors: Andrew Douglas Baxter, Cambridge (GB); David Alan Owen, Cambridge (GB); Robert John Watson, Cambridge (GB)

(73) Assignee: Darwin Discovery, Ltd. (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/830,739

(22) PCT Filed: Nov. 12, 1999

(86) PCT No.: PCT/GB99/03784

§ 371 (c)(1),
(2), (4) Date: Jun. 25, 2001

(87) PCT Pub. No.: WO00/29401

PCT Pub. Date: May 25, 2000

(30) Foreign Application Priority Data

Nov. 12, 1998 (GB) .................... PCT/GB98/03395

(51) Int. Cl.[7] ..................... C07D 309/08; A61K 31/351
(52) U.S. Cl. ..................... 514/254.1; 544/374
(58) Field of Search ................ 544/374; 514/254.1

(56) References Cited

U.S. PATENT DOCUMENTS 6,187,924 B1 * 2/2001 Baxter et al. .............. 544/374

FOREIGN PATENT DOCUMENTS

EP 0780386 6/1997
WO 9924399 5/1999

OTHER PUBLICATIONS

Close, PubMed Abstract (Ann Rheum Dis 60 Suppl 3: iii62–7), Nov. 2001.*
Creemers et al., PubMed Abstract (Circ Res 89(3): 201–10) Aug. 2001.*
Morris et al., PubMed Abstract ( Invasion Metastasis 17(6): 281–96), 1997.*
Simone, Oncology: Introduction, Cecil Textbook of Medicine, 20th Edition, vol. 1, pp. 1004–10, 1996.*
Damasio, Alzheimer's Disease and Related Dementias, Cecil Textbook of Medicine, 20th Edition, vol. 2, pp. 1992–6, 1996.*
Layzer, Degenerative Diseases of the Nervous System, Cecil Textbook of Medicine, 20th Edition, vol. 2, pp. 2050–7, 1996.*
Rasmussen et al., Matrix Metalloproteinase Inhibition as a Novel Anticancer Strategy: A Review with Special Focus on Batimastat and Marimastat, Pharmacol. Ther. vol. 75, No. 1, pp. 69–75, 1997.*
Chambers et al., Review: Changing View of the Role of Matrix Metalloproteinases in Metastasis, Journal of the National Cancer Institute, vol. 89, No. 17, Sep. 1997.*

* cited by examiner

*Primary Examiner*—Deepak Rao
(74) *Attorney, Agent, or Firm*—Saliwanchik, Lloyd & Saliwanchik

(57) ABSTRACT

4-(4-(-Chlorophenyl)piperazin-1-yl)sulfonylmethyl)-tetrahydor yran-4-carboxylic acid and the corresponding N-hydroxy amide, and derivatives thereof, are useful as therapeutic agents.

5 Claims, No Drawings

HYDROXAMIC AND CARBOXYLIC ACID DERIVATIVES HAVING MMP AND TNF INHIBITORY ACTIVITY

FIELD OF THE INVENTION

This invention relates to hydroxamic and carboxylic acid derivatives, and to their use in medicine.

BACKGROUND TO THE INVENTION

Metalloproteinases, including matrix metalloproteinases (MMps), (human fibroblast) collagenase, gelatinase and TNF convertase (TACE), and their modes of action, and also inhibitors thereof and their clinical effects, are described in WO-A-96/11209, WO-A-97/12902 and WO-A-97/19075, the contents of which are incorporated herein by reference. MMW inhibitors may also be useful in the inhibition of other marnmalian metalloproteinases such as the adamalysin family (or ADAMs) whose members include TNF convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenases, stromelysins and gelatinases, have been shown to inhibit the release of TNF both in vitro and in vivo. See Gearing etal (1994), Nature 370:555–557; McGeehan etal (1994), Nature 370:558–561; GB-A-2268934; and WO-A-93/20047. All of these reported inhibitors contain a hydroxamic acid zinc-binding group, as do the imidazole-substituted compounds disclosed in WO-A-95/23790. Other compounds that inhibit MMP and/or TNF are described in WO-A-95/13289, WO-A-96/11209, WO-A-96/035687, WO-A-96/035711, WO-A-96/035712 and WO-A-96/035714.

WO-A-99/24399 (published after the priority date claimed in this Application) discloses further compounds which are useful inhibitors of matrix metalloproteinases and/or TNFα-mediated diseases, including degenerative diseases and certain cancers. These compounds are represented by formula (I):

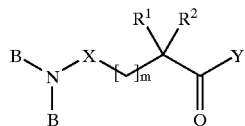

wherein
m is 0–2;
X is $S(O)_{1,2}$;
Y is OH or NHOH;
$CR^1R^2$, inter alia, is a cycloalkyl or heterocycloalkyl ring; and
B—N—B, inter alia, is an optionally-substituted heterocycloalkyl or heterocycloalkenyl ring.

SUMMARY OF THE INVENTION

The present invention relates to specific embodiments of the compounds claimed in WO-A-99/24399; see claims 1 and 2. Further, it relates to compositions and uses, as defined in claims 3–15.

DESCRIPTION OF THE INVENTION

As used in this specification, alone or in combination, the term "$C_{1-6}$alkyl" refers to straight or branched chain alkyl moiety having from one to six carbon atoms, including for example, methyl, ethyl, propyl, isopropyl, butyl, tert-butyl, pentyl, hexyl and the like.

Salts of compounds of the invention include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylarnine salts.

When the "protected carboxy" group in compounds of the invention is an esterified carboxyl group, it may be a metabolically-labile ester of formula $CO_2R^9$ where 4-tert-butylphenyl, 2,2,2-trifluoroethyl, 1-(benzyloxy)benzyl, 1-(benzyloxy)ethyl, 2-methyl-l-propionyloxypropyl, 2,4,6-trimethylbenzyloxymethyl or pivaloylmethyl group.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysins, collagenases and gelatinases. Compounds according to the invention may also exhibit in vitro inhibition of membrane shedding events known to be mediated by metalloproteinases, for example, TNF release, TNF receptor shedding, IL-6 receptor shedding, IL-1 receptor shedding, CD23 shedding and L-selectin shedding. The activity and selectivity of the compounds may be determined by use of the appropriate enzyme inhibition test, for example as described in WO-A-99/24399. They may be used and formulated as described in WO-A-099/24399, the contents of which are incorporated herein by reference.

Intermediate 1 Diethyl Tetrahydropyran-4,4-dicarboxylate

Diethyl malonate (32.0 g) was added to a solution of sodium ethoxide (1 equivalent) in ethanol and the solution was stirred for 30 min. 2-Bromoethyl ether (46.0 g) was then added and the mixture was stirred at reflux for 3 h. The mixture was then cooled, evaporated in vacuo and the residue partitioned between water and dichloromethane. The organic layer was separated and washed with water and brine, then dried ($MgSO_4$) and evaporated. The residue was then purified by flash column chromatography on silica gel, eluting with 4:1 hexanes/ether, to give the title compound (28.0 g) as colourless liquid.

$R_f$ 0.33 (4:1 hexanes/ether).

Intermediate 2 Ethyl 4-Hydroxymethyltetrahydropyran-4carboxylate

A solution of di-isobutylaluminium hydride in toluene (82 mmol) was added to a solution of intermediate 1 (9.5 g) in toluene at −40° C. over 30 min. The mixture was stirred for 1 h, then ethanol (100 ml) was added dropwise over 30 min. Sodium borohydride (2.0 g) was then added in small portions over 20 min, and the mixture stirred for 1 h. Saturated sodium sulfate (100 ml) was then added dropwise followed by ethyl acetate (200 ml). The mixture was vigorously stirred for 1 h, then filtered through Celite and the filtrate evaporated to give the title compound (5.6 g) as colourless liquid.

$R_f$ 0.60 (EtOAc).

Intermediate 3 Ethyl 4-(Methanesulfonyloxy)methyltetrahydropyran-4-carboxylate Methanesulfonyl chloride (4.6 ml) was added to a solution of intermediate 2 (1 1.0 g) at 0° C. in dichloromethane (30 ml), followed by triethylamine (8.0 ml). The mixture was stirred for 1 h, then washed with citric acid (5% aq, 30 ml), saturated sodium bicarbonate and brine. The organic layer was separated, and then dried (MgSO$_4$) and evaporated to give the title compound as colourless oil (15.2 g).

$R_f$ 0.65 (ether).

Intermediate 4 Ethyl 4-(Acetylsulfanylmethyl)tetrahydropyran-4-carboxylate

A solution of intermediate 3 (16.0 g), sodium iodide (0.2 g) and potassium thioacetate (12.0 g) in dimethylformamide (100 ml) was heated at 80° C. for 6 h. The resulting black viscous mixture was then added to aqueous bicarbonate (300 ml) and extracted with ether. The ether layer was washed with water and brine, then dried (MgSO$_4$) and evaporated. The residue was purified by flash column chromatography on silica gel, eluting with 1:1 ether/hexanes, to give the title compound (6.5 g) as pale yellow oil.

$R_f$ 0.45 (1:1 ether/hexanes).

Intermediate 5 Ethyl 4-(Chlorosulfonyl)methyltetrahydropyran-4-carbosylate

Chlorine gas was bubbled through a suspension of intermediate 4 (3.2 g) in water (100 ml) and acetic acid (5 ml) at,0° C. for 30 min. The yellow suspension was stirred at the same temperature for 30 min, then partially evaporated under vacuum and the aqueous residue extracted with dichioroinethane (100 ml). The combined organic extracts were washed with iced-cold water and brine, then dried (MgSO$_4$) and evaporated to give the title compound (3.3 g) as colourless solid.

$R_f$ 0.45 (ether).

EXAMPLE 1

Ethyl 4-(4-(4-Chlorophenyl)piperazin-1-yl)suffonylmethyl)-tetrahydropyran-4-carboxylate 4-Chlorophenylpiperazine dihydrochloride (7.3 g) and triethylamine (12 ml) were stirred in dichloromethane for 10 min, then the mixture was cooled in ice and a solution of intermediate 5 (6.9 g) in dichloromethane was added dropwise over 10 min. The mixture was stirred at 0° C. for 3 h, washed with 2% aq. citric acid, saturated sodium bicarbonate and brine, dried (MgSO$_4$) and evaporated and the residue purified by chromatography (EtOAc) to give the title compound (8.60 g) as a beige solid.

$R_f$ 0.29 (ether); MS 430 (M$^+$).

EXAMPLE 2

4-(4-(4-Chlorophenyl)piperazin-1-yl)sulfonylmethyl)-tetrahydropyran4-carboxylic Acid Lithium hydroxide (6 g) was added to a solution of example 1 (8.6 g) in methanol (150 ml) and water (100 ml) and the solution was heated under reflux for 4 h. The mixture was cooled to RT, evaporated to half volume under reduced pressure and then the solution was washed with ether. The aqueous phase was acidified with citric acid to pH 5 and extracted with dichloromethane (4 x 100 ml). The solvent was washed with brine, dried (MgSO$_4$) and evaporated to give the title compound (5.60 g, 70%) as beige solid.

$R_f$ 0.20 (EtOAc); MS 402 (M$^+$).

EXAMPPLE 3

4-(4-(4-Chlorophenyl)piperazin-1-yl)sulfonylmethyl)-tetrahydropyran-4-carboxylic Acid N-lydroxy Amide Hydrochloride Oxalyl chloride (4 ml) was added to a suspension of example 2 (5.6 g) in dichloromethane (100 ml) at 0° C., followed by dimethylforrnamide (1 drop). The mixture was stirred for 1 h, then evaporated in vacuo and the residue azeotroped with dichloromethane/hexanes (3×100 ml). The crude product was dissolved in dichloromethane (50 ml) and triethylarine (5.80 ml) and O-TBDMS hyroxylamine (2.24 g) were added. The mixture was stirred for 3 h, then washed with water, aqueous sodium bicarbonate and brine, dried and evaporated. The crude product was dissolved in dry dichloromethane (100 ml) and HCl in ether (1M, 50 mn) was added dropwise. The mixture was vigorously stirred for 30 min, then the product collected by filtration and washed with ether (2×100 ml) to give the title compound (5.0 g) as colourless powder.

$R_f$ 0.53 (10% MeOH/dichloromethane 1% NH$_4$OH); MS 418 (M$^+$).

EXAMPLE 4

4-(4-(4-Chloropheenyl)piperazin-1-yl)sulfonylmethyl)-tetrahydropyran-4-carboxylic Acid N-Hydroxy Amide The compound of Example 2 (50g) is suspended in tetrahydrofuran (500 ml) and heated to reflux. Oxalyl chloride (1 8.9g) is added in portions. The resulting mixture is stirred at reflux for at least three hours then cooled to ambient temperature giving a slurry of the acid chloride. A small addition of water in THF is added to destroy excess oxalyl chloride and the solution is stirred out overnight.

A solution of tetrahydrofuran (100 ml) and 50% aqueous hydroxylamine 50 ml) is prepared and cooled to 0.5° C. The slurry of acid chloride in tetrahydrofuran is added to the hydroxylamine solution in proportions maintaining the temperature at less than 20° C. On completion of the addition the mixture is stirred at ambient temperature for 1 hour and then tetrahydrofuran removed by atmospheric distillation. The volume is maintained by the addition of water (600 ml). The atmospheric removal of THF is continued until a head temperature of approximately 70° C. is attained. Heating is stopped and the resulting aqueous suspension cooled slowly to 10–20° C. The mixture is adjusted to pH 7.5–8.5 by the addition of dilute aqueous ammonia and stirred overnight. The product is isolated by filtration. The cake is washed with water (400 ml) and dried at 35–45° C. to give the title compound (45g, 87%) as a white to off-white solid.

What is claimed is:

1. A compound, 4-(4-(4-Chlorophenyl)piperazin-1-yl)sulfonylmethyl)-tetrahydropyran-4-carboxylic acid N-hydroxy amide or a salt, solvate, hydrate, N-oxide, protected amino, or protected hydroxamic acid derivative thereof.

2. A compound, 4(4(4-Chlorophenyl)piperazin-1-yl)sulfonylmethyl)-tetrahydropyran-4-carboxylic acid or a salt, solvate, hydrate, N-oxide, protected amino or protected carboxy derivative thereof.

3. A compound, 4-(4-(4-Chlorophenyl)piperazin-1-yl)sulfonylmethyl)-tetrahydropyran-4-carboxylic acid N-hydroxy amide hydrochloride or a solvate, hydrate, N-oxide, protected amino, or protected hydroamic acid derivative thereof.

4. A pharmaceutical composition for use in therapy comprising a compound and a phannaceutically-acceptable diluent or carrier, wherein said compound is 4-(4-(4Chlorophenyl)piperazin-1-yl)sulfonylmethyl)-tetrahydropyran-4-carboxylic acid N-hydroxy amide or a salt, solvate, hydrate, N-oxide, protected amino, or protected hydroxamic acid derivative thereof.

5. A pharmaceutical composition for use in therapy comprising a compound and a pharmaceutically-acceptable diluent or carrier, wherein said compound is 4-(4-(4Chlorophenyl)piperazin-1-yl)sulfonylmethyl)-tetrahydropyran-4-carboxylic acid or a salt, solvate, hydrate, N-oxide, protected amino or protected carboxy derivative thereof.

\* \* \* \* \*

UNITED STATES PATENT AND TRADEMARK OFFICE
CERTIFICATE OF CORRECTION

PATENT NO.    : 6,706,719 B1
DATED         : March 16, 2004
INVENTOR(S)   : Andrew Douglas Baxter et al.

It is certified that error appears in the above-identified patent and that said Letters Patent is hereby corrected as shown below:

Column 4,
Line 61, "4(4(4-Chlorophenyl)" should read -- 4-(4-(4-Chlorophenyl) --.

Column 5,
Line 4, "phannaceutically-" should read -- pharmaceutically- --.
Line 6, "(4Chlorophenyl);" should read -- (4-Chlorophenyl) --.

Column 6,
Line 4, "(4Chlorophenyl);" should read -- (4-Chlorophenyl) --.

Signed and Sealed this

Twenty-ninth Day of November, 2005

JON W. DUDAS
*Director of the United States Patent and Trademark Office*